US00PP31596P2

(12) United States Plant Patent
Rijk

(10) Patent No.: US PP31,596 P2
(45) Date of Patent: Mar. 24, 2020

(54) ***DAHLIA* PLANT NAMED 'DODAHHYPNORE 19'**

(50) Latin Name: *Dahlia variabilis*
Varietal Denomination: Dodahhypnore 19

(71) Applicant: DUMMEN GROUP B.V., De Lier (NL)

(72) Inventor: Nadine Rijk, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/501,225

(22) Filed: Mar. 9, 2019

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./321
CPC ..... A01H 5/02; A01H 6/14
See application file for complete search history.

*Primary Examiner* — Annette H Para
(74) *Attorney, Agent, or Firm* — C. A. Whealy

(57) ABSTRACT

A new and distinct cultivar of *Dahlia* plant named 'Dodahhypnore 19', characterized by its relatively compact, broadly upright and uniformly mounding plant habit; relatively small dark green-colored leaves; early and freely flowering habit; medium to large inflorescences with red-colored ray florets; and good postproduction longevity.

2 Drawing Sheets

Botanical designation: *Dahlia variabilis.*
Cultivar denomination: 'DODAHHYPNORE 19'.

BACKGROUND OF THE INVENTION

The present invention relates to a new and distinct cultivar of *Dahlia* plant, botanically known as *Dahlia variabilis* and hereinafter referred to by the name 'Dodahhypnore 19'.

The new *Dahlia* plant is a product of a planned breeding program conducted by the Inventor in De Lier, The Netherlands. The objective of the breeding program is to create new container *Dahlia* plants that have a freely branching and flowering habit, dark-colored leaves, large attractive inflorescences and good postproduction longevity.

The new *Dahlia* plant originated from a cross-pollination in Hillegom, The Netherlands of two unidentified proprietary selections of *Dahlia variabilis*, not patented. The new *Dahlia* plant was discovered and selected by the Inventor as a single flowering plant from within the progeny of the stated cross-pollination in a controlled greenhouse environment in De Lier, The Netherlands during the spring of 2015.

Asexual reproduction of the new *Dahlia* plant by vegetative terminal cuttings in a controlled greenhouse environment in De Lier, The Netherlands since the spring of 2015 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dodahhypnore 19'. These characteristics in combination distinguish 'Dodahhypnore 19' as a new and distinct *Dahlia* plant:

1. Relatively compact, broadly upright and uniformly mounding plant habit.
2. Relatively small dark green-colored leaves.
3. Early and freely flowering habit.
4. Medium to large inflorescences with red-colored ray florets.
5. Good postproduction longevity.

Compared to plants of the parent selections, plants of the new *Dahlia* differ primarily in growth habit as plants of the new *Dahlia* are more uniformly mounding than plants of the parent selections.

Plants of the new *Dahlia* can be compared to plants of *Dahlia* 'Fidahhypre', disclosed in U.S. Plant Pat. No. 21,252. In side-by-side comparisons, plants of the new *Dahlia* differ primarily from plants of 'Fidahhypre' in the following characteristics:

1. Plants of the new *Dahlia* are more uniform than plants of 'Fidahhypre'.
2. Ray florets of plants of the new *Dahlia* are darker red than ray florets of plants of 'Fidahhypre'.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph on the first sheet is a side perspective view of a typical flowering plant of 'Dodahhypnore 19' grown in a container.

The photograph on the second sheet is a close-up view of a typical inflorescence of 'Dodahhypnore 19'.

DETAILED BOTANICAL DESCRIPTION

The aforementioned photographs and the following observations and measurements describe plants grown during the late summer and early autumn in 13-cm containers in a glass-covered greenhouse in De Lier, The Netherlands and under environmental conditions and cultural practices which approximate those generally used in commercial potted *Dahlia* production. During the production of the plants, day temperatures ranged from 24° C. to 30° C., night temperatures ranged from 18° C. to 20° C. and light levels averaged 600 watt/$m^2$. Plants were ten weeks old when the photographs and description were taken. In the following description, color references are made to The Royal Horticultural Society Colour Chart, 2007 Edition, except where general terms of ordinary dictionary significance are used.

Botanical classification: *Dahlia variabilis* 'Dodahhypnore 19'.

Parentage:

*Female, or seed, parent*.—Unidentified proprietary selection of *Dahlia variabilis*, not patented.

*Male, or pollen, parent*.—Unidentified proprietary selection of *Dahlia variabilis*, not patented.

Propagation:

*Type*.—By vegetative terminal cuttings.

*Time to initiate roots, summer*.—About twelve days at temperatures about 22° C. to 30° C.

*Time to initiate roots, winter*.—About two weeks at temperatures about 22° C. to 30° C.

*Time to produce a rooted plant, summer*.—About two weeks at temperatures about 22° C. to 30° C.

*Time to produce a rooted plant, winter*.—About 2.5 weeks at temperatures about 20° C. to 22° C.

*Root description*.—Medium in thickness, fibrous; typically whitish grey in color, actual color of the roots is dependent on substrate composition, water quality, fertilizers, substrate temperature and age of roots; tuber development has not been observed on plants of the new *Dahlia*.

*Rooting habit*.—Moderately freely branching; medium density.

Plant description:

*Plant and growth habit*.—Relatively compact, broadly upright and uniformly mounding plant form; broad inverted triangle; moderately freely basal branching with about three primary lateral branches developing per plant, each primary lateral branch with about 10 to 13 secondary branches; inflorescences held above the foliar plane on strong peduncles; bushy and dense habit; moderately vigorous growth habit and moderate growth rate.

*Plant height, soil level to top of foliar plane*.—About 22 cm.

*Plant height, soil level to top of floral plane*.—About 34 cm.

*Plant diameter or spread*.—About 27 cm.

*Lateral branches*.—Length: About 15 cm to 17 cm. Diameter: About 1.5 cm. Internode length: About 1.5 cm. Aspect: Erect to somewhat outwardly spreading. Strength: Moderately strong. Texture and luster: Smooth, glabrous; semi-glossy. Color: Close to 146B.

Leaf description:

*Arrangement*.—Opposite; leaves may be single or compound with three or occasionally five leaflets.

*Leaf length*.—About 13 cm to 17 cm.

*Leaf width*.—About 10 cm to 12 cm.

*Leaflet length*.—About 5 cm to 7 cm.

*Leaflet width*.—About 3 cm to 4 cm.

*Leaf and leaflet shape*.—Ovate.

*Leaf and leaflet apex*.—Acute.

*Leaf and leaflet base*.—Attenuate.

*Leaf and leaflet margin*.—Serrate to dentate.

*Leaf and leaflet venation pattern*.—Pinnate.

*Leaf and leaflet texture and luster, upper surface*.—Sparsely pubescent; slightly rough; slightly glossy.

*Leaf and leaflet texture and luster, lower surface*.—Sparsely pubescent; slightly rough; matte.

*Color*.—Developing and fully expanded leaves and leaflets, upper surface: Close to 147A; venation, close to 147B. Developing and fully expanded leaves and leaflets, lower surface: Close to 148B; venation, close to 148A.

*Petioles*.—Length: About 3.5 cm to 4.5 cm. Diameter: About 4 mm. Strength: Moderately strong. Texture and luster, upper and lower surfaces: Smooth, glabrous; slightly glossy. Color, upper surface: Close to 144C. Color, lower surface: Close to 144B.

Inflorescence description:

*Appearance and arrangement*.—Double inflorescence form with ray florets forming acropetally on a receptacle; inflorescences positioned above the foliar plane on strong peduncles; inflorescences face mostly upright; freely flowering habit with about ten inflorescences per plant.

*Fragrance*.—None detected.

*Time to flower*.—Plants flower continuously from spring through the autumn in The Netherlands; early flowering habit, plants begin flowering about 50 to 60 days after planting.

*Post-production longevity*.—Inflorescences maintain good substance for about two weeks on the plant; inflorescences persistent.

*Inflorescence buds*.—Height: About 7 mm. Diameter: About 1 cm. Shape: Globular, flattened. Texture and luster: Smooth; semi-glossy. Color: Close to 144B.

*Inflorescence size*.—Diameter: About 6 cm to 8 cm. Depth (height): About 10 cm to 13 cm. Disc diameter: About 1 cm. Receptacle height: About 4 mm. Receptacle diameter: About 1.8 cm. Receptacle color: Close to 146A.

*Ray florets*.—Quantity per inflorescence: About 60 to 70 arranged in about eight whorls. Length: About 3.5 cm. Width: About 1.4 cm. Shape: Lanceolate. Apex: Obtuse. Base: Cuneate. Margin: Entire. Aspect: Initially upright to roughly perpendicular to the peduncle; somewhat concave. Texture and luster, upper and lower surfaces: Smooth, glabrous; matte. Color: When opening, upper and lower surfaces: Close to 46A. Fully opened, upper surface: Close to 42A; venation, close to 42A; color does not change with development. Fully opened, lower surface: Close to 42B; venation, close to 42B; color does not change with development.

*Disc florets*.—Quantity per inflorescence: About 10 to 15 arranged in about four to six whorls. Length: About 1.2 cm. Diameter: About 2 mm. Shape: Tubular, elongated; apices obtuse. Texture and luster: Smooth, glabrous; matte. Color, when opening and fully opened: Close to 1B.

*Phyllaries*.—Quantity per inflorescence: About five arranged in a single whorl. Length: About 1.3 cm. Width: About 6 mm. Shape: Ovate. Apex: Acute. Base: Cuneate. Margin: Entire. Texture and luster, upper and lower surfaces: Smooth, glabrous; matte. Color, upper surface: Close to 137A; venation, close to 137A. Color, lower surface: Close to 137B; venation, close to 137B.

*Peduncles*.—Length, terminal peduncle: About 8 cm to 12 cm. Diameter, terminal peduncle: About 4 mm. Aspect: Mostly erect. Strength: Strong. Texture and luster: Smooth, glabrous; semi-glossy. Color: Close to 144A.

*Reproductive organs*.—Androecium: Present on disc florets only. Quantity per floret: One. Filament length: About 4 mm. Filament color: Close to 17A. Anther shape: Narrowly elliptic. Anther size: About 9 mm by 1.5 mm. Anther color: Close to 6A. Pollen amount: Moderate. Pollen color: Close to 17B. Gynoecium: Present on disc florets only. Quantity per floret: One. Style length: About 3 mm. Style color: Close to 2A. Stigma diameter: About 3 mm. Stigma color: Close to 7A. Ovary color: Close to 145C. Seeds: To date, seed development has not been observed on plants of the new *Dahlia*.

Pathogen & pest resistance: To date, plants of the new *Dahlia* have not been observed to be resistant to pathogens and pests common to *Dahlia* plants.

Temperature tolerance: Plants of the new *Dahlia* tolerate high temperatures about 35° C. and short periods of low temperatures about 5° to 10° C.

It is claimed:

1. A new and distinct *Dahlia* plant named 'Dodahhypnore 19' as illustrated and described.

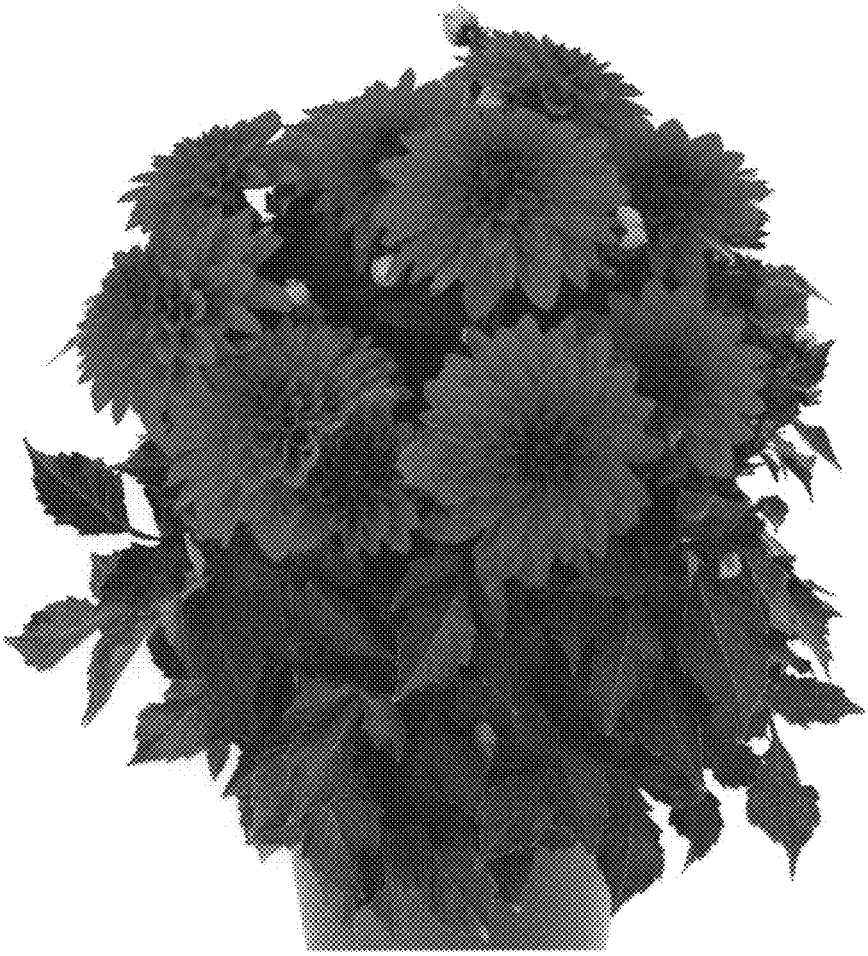

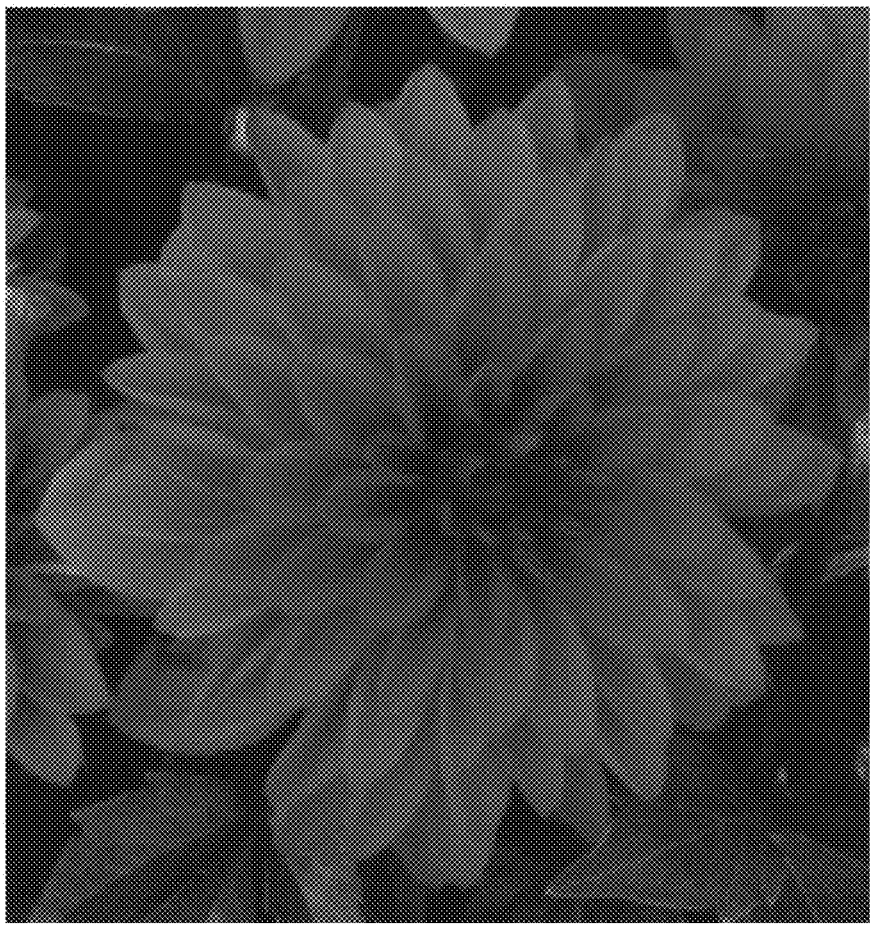

* * * * *